United States Patent
Komurasaki et al.

(10) Patent No.: US 9,427,473 B2
(45) Date of Patent: Aug. 30, 2016

(54) AQUEOUS OPHTHALMIC COMPOSITION

(71) Applicant: ROHTO PHARMACEUTICAL CO., LTD., Osaka-shi, Osaka (JP)

(72) Inventors: Ryo Komurasaki, Osaka (JP); Yoko Mizutare, Osaka (JP); Atsuko Nakata, Osaka (JP)

(73) Assignee: ROHTO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 14/384,810

(22) PCT Filed: Nov. 29, 2013

(86) PCT No.: PCT/JP2013/082188
§ 371 (c)(1),
(2) Date: Sep. 12, 2014

(87) PCT Pub. No.: WO2014/087931
PCT Pub. Date: Jun. 12, 2014

(65) Prior Publication Data
US 2015/0018416 A1 Jan. 15, 2015

(30) Foreign Application Priority Data
Dec. 4, 2012 (JP) .............................. P2012-265841

(51) Int. Cl.
| | | |
|---|---|---|
| A61K 31/07 | (2006.01) | |
| A61K 31/23 | (2006.01) | |
| A61K 47/44 | (2006.01) | |
| A61K 47/10 | (2006.01) | |
| A61K 47/14 | (2006.01) | |
| A61K 9/00 | (2006.01) | |
| A01N 25/22 | (2006.01) | |
| A01N 37/36 | (2006.01) | |

(52) U.S. Cl.
CPC ............... *A61K 47/44* (2013.01); *A01N 25/22* (2013.01); *A01N 37/36* (2013.01); *A61K 9/0048* (2013.01); *A61K 31/07* (2013.01); *A61K 31/23* (2013.01); *A61K 47/10* (2013.01); *A61K 47/14* (2013.01)

(58) Field of Classification Search
CPC .............................. A61K 31/07; A61K 31/23
See application file for complete search history.

(56) References Cited

U.S. PATENT DOCUMENTS

2006/0083733 A1 4/2006 Nishio
2012/0108658 A1* 5/2012 Odaka .................. A61K 9/0048
514/458

FOREIGN PATENT DOCUMENTS

| CN | 1849111 A | 10/2006 |
|---|---|---|
| EP | 1666027 | 6/2006 |
| JP | 2005-298448 A | 10/2005 |
| JP | 2006-117656 A | 11/2006 |
| JP | 2008-222638 A | 9/2008 |
| JP | 2009-073788 A | 4/2009 |
| JP | 2009-173638 A | 8/2009 |
| JP | 2010-120930 A | 6/2010 |
| JP | 2013-144671 A | 7/2013 |
| JP | 2013-256475 A | 12/2013 |
| WO | 2012/090985 A1 | 7/2012 |
| WO | 2013/008715 A1 | 1/2013 |

OTHER PUBLICATIONS

International Search Report issued in corresponding International Patent Application No. PCT/JP2013/082188 dated Jan. 21, 2014.
International Preliminary Report on Patentability and Written Opinion issued in corresponding International Patent Application No. PCT/JP2013/082188 dated Jun. 18, 2015.
Notice of Allowance issued in counterpart Japanese Patent Application No. P2014-551072 dated Jan. 12, 2016.
Jihua et al., "General Guidelines for Practitioner Treatment," Jiangsu Science and Technology Press, 1: 387-388 (2012) (partial English translation).
Bingyi, "Handbook of Encyclopedia of Cosmetics Chemical and Technology," China Light Industry Press, 2: 825 (2000) (partial English translation).
Limin, "Classification and Application Technologies of Defoamers," Surfactant Soap and Detergent, 3: 70-73 (2009).

* cited by examiner

*Primary Examiner* — Zohreh Fay
(74) *Attorney, Agent, or Firm* — Morgan, Lewis & Bockius LLP (57) ABSTRACT

The present invention relates to an aqueous ophthalmic composition comprising (A) polyoxyethylene castor oil, (B) polyethylene glycol monostearate, and (C) at least one member selected from the group consisting of sesame oil, castor oil, vitamin A, and chlorobutanol.

18 Claims, 1 Drawing Sheet

AQUEOUS OPHTHALMIC COMPOSITION

TECHNICAL FIELD

The present invention relates to an aqueous ophthalmic composition. More specifically, the present invention relates to an aqueous ophthalmic composition having reduced foaming and a reduced defoaming time.

BACKGROUND ART

For dissolution of components with relatively low water-solubility and other purposes, solubilizing agents are added to many aqueous ophthalmic formulations. A surfactant can be given as an example of the solubilizing agents used in the field of ophthalmology. It is known that polyoxyethylene castor oil is a nonionic surfactant and is added to an aqueous ophthalmic composition for helping dissolution of other components and other purposes (Patent Literature 1). It is known that polyethylene glycol monostearate is also a type of nonionic surfactant and is added to an aqueous ophthalmic composition for helping dissolution of other components and other purposes.

However, an aqueous composition containing a surfactant is known to easily foaming, and foam is inevitably generated when vibration or impact is applied during production or distribution. In general, to use the aqueous ophthalmic composition in a manner safe on the eyes, dissolution check and foreign matter detection are required in the production steps. However, when foam is generated in the aqueous ophthalmic composition during production, and disappears at low speed, it is hard to distinguish a foreign matter or the like from the foam. Consequently, steps such as dissolution check and foreign matter detection take a long period of time, which may cause a problem of preventing efficient production.

On the other hand, a variety of active components or additives are generally added to an aqueous ophthalmic composition depending on the intended purpose. For example, as a method for stabilizing the viscosity of a composition, there is disclosed a composition that is applicable to mucous membranes, which contains vegetable oil such as sesame oil or castor oil (Patent Literature 2). Vitamins A have been added to an ophthalmic composition ever before for purposes such as reducing eyestrain by promoting eye cell metabolism and respiration, and exhibiting anti-inflammatory action (Patent Literature 3). Chlorobutanol is also known as an additive for an aqueous ophthalmic composition.

However, an effect on an aqueous ophthalmic composition provided when these components and a specific surfactant are added to the aqueous ophthalmic composition cannot be easily predicted.

CITATION LIST

Patent Literatures

Patent Literature 1: JP 2005-298448 A
Patent Literature 2: JP 2006-117656 A
Patent Literature 3: JP 2009-173638 A

SUMMARY OF INVENTION

Problems to be Solved by the Invention

The present inventors have found a new problem in that particularly, an aqueous ophthalmic composition containing both polyoxyethylene castor oil and polyethylene glycol monostearate can easily foam, and the resulting foam is hard to disappear. It is an object of the present invention to provide an aqueous ophthalmic composition and the like having less generation of foaming due to vibration or impact and a reduced defoaming time even when foam is once generated for the aqueous ophthalmic composition that easily generates foam.

Means for Solving the Problems

As a result of extensive research to solve the above problems, the present inventors have found that when an aqueous ophthalmic composition containing polyoxyethylene castor oil (hereinafter sometimes referred to as "component (A)") and polyethylene glycol monostearate (hereinafter sometimes referred to as "component (B)" or "polyoxyl stearate") is supplemented with at least one member selected from the group consisting of sesame oil, castor oil, vitamin A, and chlorobutanol (hereinafter sometimes referred to as "component (C)"), foam generated due to vibration or impact can be reduced during production and distribution, and the time taken for the generated foam to disappear can be significantly reduced.

Accordingly, for example, the present invention provides a new aqueous ophthalmic composition as stated below.

Item 1-1. An aqueous ophthalmic composition, comprising (A) polyoxyethylene castor oil, (B) polyethylene glycol monostearate, and (C) at least one member selected from the group consisting of sesame oil, castor oil, vitamin A, and chlorobutanol.

Item 1-2. The aqueous ophthalmic composition according to Item 1-1, wherein component (A) is polyoxyethylene castor oil in which the average number of moles of added ethylene oxide is 2 to 70.

Item 1-3. The aqueous ophthalmic composition according to Item 1-1 or 1-2, wherein component (B) is polyethylene glycol monostearate in which the average number of moles of added ethylene oxide is 2 to 150.

Item 1-4. The aqueous ophthalmic composition according to any one of Items 1-1 to 1-3, wherein the total content of component (A) is 0.0001 to 5 w/v % based on the total amount of the aqueous ophthalmic composition.

Item 1-5. The aqueous ophthalmic composition according to any one of Items 1-1 to 1-4, wherein the total content of component (B) is 0.0001 to 5 w/v % based on the total amount of the aqueous ophthalmic composition.

Item 1-6. The aqueous ophthalmic composition according to any one of Items 1-1 to 1-5, wherein the total content of component (B) is 0.001 to 100 parts by weight based on 1 part by weight of the total content of component (A).

Item 1-7. The aqueous ophthalmic composition according to any one of Items 1-1 to 1-6, wherein the total content of component (C) is 0.0001 to 5 w/v % based on the total amount of the aqueous ophthalmic composition.

Item 1-8. The aqueous ophthalmic composition according to any one of Items 1-1 to 1-7, wherein the total content of component (C) is 0.00002 to 10,000 parts by weight based on 1 part by weight of the total content of component (A).

Item 1-9. The aqueous ophthalmic composition according to any one of Items 1-1 to 1-8, wherein the total content of component (C) is 0.00002 to 10,000 parts by weight based on 1 part by weight of the total content of component (B).

Item 1-10. The aqueous ophthalmic composition according to any one of Items 1-1 to 1-9, further comprising (D) a buffer.

Item 1-11. The aqueous ophthalmic composition according to Item 1-10, wherein the total content of component (D) is 0.01 to 20 w/v % based on the total amount of the aqueous ophthalmic composition.

Item 1-12. The aqueous ophthalmic composition according to any one of Items 1-1 to 1-11, further comprising a surfactant other than components (A) and (B) as a component (E).

Item 1-13. The aqueous ophthalmic composition according to Item 1-12, wherein component (E) is at least one member selected from the group consisting of polyoxyethylene sorbitan fatty acid ester, polyoxyethylene hydrogenated castor oil, and a polyoxyethylene-polyoxypropylene block copolymer.

Item 1-14. The aqueous ophthalmic composition according to Item 1-12 or 1-13, wherein the total content of component (E) is 0.0001 to 5 w/v % based on the total amount of the aqueous ophthalmic composition.

Item 1-15. The aqueous ophthalmic composition according to any one of Items 1-1 to 1-14, wherein the aqueous ophthalmic composition is eye drops.

Item 1-16. The aqueous ophthalmic composition according to any one of Items 1-1 to 1-14, wherein the aqueous ophthalmic composition is an eye wash.

Item 1-17. The aqueous ophthalmic composition according to any one of Items 1-1 to 1-14, wherein the aqueous ophthalmic composition is a solution for wearing a contact lens.

Item 1-18. The aqueous ophthalmic composition according to any one of Items 1-1 to 1-14, wherein the aqueous ophthalmic composition is a contact lens care solution.

Item 1-19. The aqueous ophthalmic composition according to any one of Items 1-1 to 1-18, wherein the aqueous ophthalmic composition is for dry eyes or for relieving eye dryness.

For example, the present invention also provides methods for reducing foaming of an aqueous ophthalmic composition according to the following embodiments.

Item 2-1. A method for reducing foaming of an aqueous ophthalmic composition, comprising adding (A) polyoxyethylene castor oil, (B) polyethylene glycol monostearate, and (C) at least one member selected from the group consisting of sesame oil, castor oil, vitamin A, and chlorobutanol to the aqueous ophthalmic composition.

Item 2-2. A method for reducing foaming of an aqueous ophthalmic composition, comprising supplementing an aqueous ophthalmic composition comprising (A) polyoxyethylene castor oil and (B) polyethylene glycol monostearate with (C) at least one member selected from the group consisting of sesame oil, castor oil, vitamin A, and chlorobutanol.

For example, the present invention also provides methods for reducing defoaming time in an aqueous ophthalmic composition and methods for reducing variations in the drip amount of an aqueous ophthalmic composition during use according to the following embodiments.

Item 3-1. A method for reducing defoaming time in an aqueous ophthalmic composition, comprising adding (A) polyoxyethylene castor oil, (B) polyethylene glycol monostearate, and (C) at least one member selected from the group consisting of sesame oil, castor oil, vitamin A, and chlorobutanol to the aqueous ophthalmic composition.

Item 3-2. A method for reducing defoaming time in an aqueous ophthalmic composition, comprising supplementing an aqueous ophthalmic composition comprising (A) polyoxyethylene castor oil and (B) polyethylene glycol monostearate with (C) at least one member selected from the group consisting of sesame oil, castor oil, vitamin A, and chlorobutanol.

Item 3-3. A method for reducing variations in the drip amount of an aqueous ophthalmic composition during use, comprising adding (A) polyoxyethylene castor oil, (B) polyethylene glycol monostearate, and (C) at least one member selected from the group consisting of sesame oil, castor oil, vitamin A, and chlorobutanol to the aqueous ophthalmic composition.

Item 3-4. A method for reducing variations in the drip amount of an aqueous ophthalmic composition during use, comprising supplementing an aqueous ophthalmic composition comprising (A) polyoxyethylene castor oil and (B) polyethylene glycol monostearate with (C) at least one member selected from the group consisting of sesame oil, castor oil, vitamin A, and chlorobutanol.

For example, the present invention also provides a method for enhancing antimicrobial effectiveness of an aqueous ophthalmic composition according to the following embodiment.

Item 4. A method for enhancing antimicrobial effectiveness of an aqueous ophthalmic composition, comprising adding (A) polyoxyethylene castor oil, (B) polyethylene glycol monostearate, and (C) at least one member selected from the group consisting of sesame oil, castor oil, vitamin A, and chlorobutanol to the aqueous ophthalmic composition.

For example, the present invention further provides a method for imparting an effect of stabilizing tears to an aqueous ophthalmic composition or a method for imparting an effect of spreading a tear film lipid layer to an aqueous ophthalmic composition according to the following embodiment.

Item 5-1. A method for imparting an effect of stabilizing tears to an aqueous ophthalmic composition, comprising adding (A) polyoxyethylene castor oil, (B) polyethylene glycol monostearate, and (C) at least one member selected from the group consisting of sesame oil, castor oil, vitamin A, and chlorobutanol to the aqueous ophthalmic composition.

Item 5-2. A method for imparting an effect of spreading a tear film lipid layer to an aqueous ophthalmic composition, comprising adding (A) polyoxyethylene castor oil, (B) polyethylene glycol monostearate, and (C) at least one member selected from the group consisting of sesame oil, castor oil, vitamin A, and chlorobutanol to the aqueous ophthalmic composition.

For example, the present invention further provides methods for reducing the odor of an aqueous ophthalmic composition according to the following embodiments.

Item 6-1. A method for reducing odor of an aqueous ophthalmic composition, comprising adding (A) polyoxyethylene castor oil, (B) polyethylene glycol monostearate, and (C) at least one member selected from the group consisting of sesame oil, castor oil, vitamin A, and chlorobutanol to the aqueous ophthalmic composition.

Item 6-2. A method for reducing odor of an aqueous ophthalmic composition, comprising supplementing an aqueous ophthalmic composition comprising (A) polyoxyethylene castor oil and (B) polyethylene glycol monostearate with (C) at least one member selected from the group consisting of sesame oil, castor oil, vitamin A, and chlorobutanol.

For example, the present invention also provides use according to the following embodiments.

Item 7-1. Use of (A) polyoxyethylene castor oil, (B) polyethylene glycol monostearate, and (C) at least one member selected from the group consisting of sesame oil, castor oil, vitamin A, and chlorobutanol for production of an aqueous ophthalmic composition.

Item 7-2. The use according to Item 7-1, wherein the aqueous ophthalmic composition is the composition according to any one of Items 1-1 to 1-18.

For example, the present invention also provides use according to the following embodiments.

Item 8-1. Use of a composition as an aqueous ophthalmic composition, the composition comprising (A) polyoxyethylene castor oil, (B) polyethylene glycol monostearate, and (C) at least one member selected from the group consisting of sesame oil, castor oil, vitamin A, and chlorobutanol.

Item 8-2. The use according to Item 8-1, wherein the composition is the composition according to any one of Items 1-1 to 1-18.

For example, the present invention also provides compositions according to the following embodiments.

Item 9-1. A composition for use as an aqueous ophthalmic composition, the composition comprising (A) polyoxyethylene castor oil, (B) polyethylene glycol monostearate, and (C) at least one member selected from the group consisting of sesame oil, castor oil, vitamin A, and chlorobutanol.

Item 9-2. The composition according to Item 9-1, which is recited in any one of Items 1-1 to 1-18.

For example, the present invention also provides methods for producing an aqueous ophthalmic composition according to the following embodiments.

Item 10-1. A method for producing an aqueous ophthalmic composition, comprising the step of mixing water with (A) polyoxyethylene castor oil, (B) polyethylene glycol monostearate, and (C) at least one member selected from the group consisting of sesame oil, castor oil, vitamin A, and chlorobutanol.

Item 10-2. The method according to Item 10-1, wherein the aqueous ophthalmic composition is the composition according to any one of Items 1-1 to 1-18.

Effects of the Invention

According to the present invention, the addition of polyoxyethylene castor oil, polyethylene glycol monostearate, and at least one member selected from the group consisting of sesame oil, castor oil, vitamin A, and chlorobutanol to an aqueous ophthalmic composition makes it possible to reduce the generation of foam due to vibration or impact during production and distribution and to significantly reduce the time taken for the generated foam to disappear. This makes it easy to distinguish foreign matter or the like from the foam and makes it possible to reduce the time required for steps such as dissolution check and foreign matter detection, so that production efficiency can be significantly improved.

The reduction of foam of the aqueous ophthalmic composition to be generated can reduce variations in the amount of the composition used each time, so that the user can easily control the amount of use each time and easily handle the composition particularly when the composition is eye drops or a solution for wearing a contact lens, which is used in a relatively small amount each time. This improves compliance, which is advantageous particularly when the aqueous ophthalmic composition is a pharmaceutical or the like.

As another advantageous effect, the aqueous ophthalmic composition of the present invention also attains the effect of significantly stabilizing the tear film, in other words, the effect of stabilizing the tear. Therefore, the aqueous ophthalmic composition of the present invention can suppress the breaking up of the tear film and is particularly useful as eye drops, an eye wash, a solution for wearing a contact lens, a contact lens care solution, or the like, which is used for the purpose of relieving dry eyes or eye dryness.

As a further advantageous effect, the aqueous ophthalmic composition of the present invention attains the effect of significantly enhancing antimicrobial effectiveness. This makes the aqueous ophthalmic composition resistant to spoilage caused by microbial contamination or the like after being opened. Therefore, the composition of the present invention is useful as a multidose aqueous ophthalmic composition, which is repeatedly used after being opened. In particular, the composition of the present invention is useful as eye drops, an eye wash, a solution for wearing a contact lens, a contact lens care solution, or the like, which can hardly contain a large amount of an antiseptic in view of safety although it is required to have high antimicrobial effectiveness for hygiene.

The present invention is also highly effective in spreading a tear film lipid layer. After the instillation of the composition of the present invention, therefore, the composition can quickly spread over the surface of the cornea without destroying the tear film. Thus, the oil components contained in the aqueous ophthalmic composition can quickly spread in the form of a lipid layer without forming oil droplets on the surface of the tear when the composition is instilled. This makes it possible to effectively and quickly produce the effect of suppressing the evaporation of the tear. The composition of the present invention is particularly useful as eye drops, an eye wash, a solution for wearing a contact lens, a contact lens care solution, or the like, which is used for the purpose of relieving dry eyes or eye dryness.

As a further advantageous effect, the present invention also attains the effect of reducing the distinctive odor of polyoxyethylene castor oil and polyethylene glycol monostearate. Therefore, the user can comfortably use the aqueous ophthalmic composition for a long period of time, which can improve compliance. This is particularly advantageous when the aqueous ophthalmic composition is a pharmaceutical or the like.

The aqueous ophthalmic composition of the present invention has the aforementioned various excellent effects and can be effectively used for a long period of time in a safer and more comfortable manner.

EMBODIMENTS FOR CARRYING OUT THE INVENTION

1. Aqueous Ophthalmic Composition

The aqueous ophthalmic composition of the present invention contains (A) polyoxyethylene castor oil, (B) polyethylene glycol monostearate, and (C) at least one member selected from the group consisting of sesame oil, castor oil, vitamin A, and chlorobutanol.

The aqueous ophthalmic composition of the present specification indicates an ophthalmic composition in which the content of water exceeds 40 w/v % or more based on the total amount of the aqueous ophthalmic composition. The content of water in the aqueous ophthalmic composition is preferably 85 w/v % or more, more preferably 90 w/v % or more, even more preferably 92 w/v % or more, and particularly preferably 95 w/v % or more.

In the present specification, the unit of content "%" indicates "w/v %" and is the same as "g/100 mL".

In the present specification, the abbreviation "POE" means polyoxyethylene unless otherwise specified.

In the present specification, the abbreviation "POP" means polyoxypropylene unless otherwise specified.

In the present specification, contact lenses include all kinds of contact lenses including hard lenses, oxygen-permeable hard lenses, soft lenses (including silicone hydrogel lenses), and color lenses unless otherwise specified.

Hereinafter, the present invention will be specifically described.

(1) Polyoxyethylene Castor Oil

The aqueous ophthalmic composition of the present invention contains polyoxyethylene castor oil (component (A)). By using the component (A) in combination with (B) polyethylene glycol monostearate and (C) at least one member selected from the group consisting of sesame oil, castor oil, vitamin A, and chlorobutanol, which are described below, the excellent effect of the present invention as described above is exhibited.

Polyoxyethylene castor oil is a known compound obtained by addition polymerization of ethylene oxide with castor oil, and several kinds of polyoxyethylene castor oils having a different average number of moles of added ethylene oxide are known. In the present invention, the average number of moles of added ethylene oxide in the polyoxyethylene castor oil used as the component (A) is not particularly limited. For example, the average number of moles of added ethylene oxide is about 2 to 70. Specific examples include polyoxyethylene castor oil 3 in which the average number of moles of added ethylene oxide is 3, polyoxyethylene castor oil 4 in which the average number of moles of added ethylene oxide is 4, polyoxyethylene castor oil 6 in which the average number of moles of added ethylene oxide is 6, polyoxyethylene castor oil 7 in which the average number of moles of added ethylene oxide is 7, polyoxyethylene castor oil 10 in which the average number of moles of added ethylene oxide is 10, polyoxyethylene castor oil 13.5 in which the average number of moles of added ethylene oxide is 13.5, polyoxyethylene castor oil 17 in which the average number of moles of added ethylene oxide is 17, polyoxyethylene castor oil 20 in which the average number of moles of added ethylene oxide is 20, polyoxyethylene castor oil 25 in which the average number of moles of added ethylene oxide is 25, polyoxyethylene castor oil 30 in which the average number of moles of added ethylene oxide is 30, polyoxyethylene castor oil 35 in which the average number of moles of added ethylene oxide is 35, polyoxyethylene castor oil 40 in which the average number of moles of added ethylene oxide is 40, polyoxyethylene castor oil 50 in which the average number of moles of added ethylene oxide is 50, polyoxyethylene castor oil 60 in which the average number of moles of added ethylene oxide is 60, and polyoxyethylene castor oil 70 in which the average number of moles of added ethylene oxide is 70.

Of these, polyoxyethylene castor oil in which the average number of moles of added ethylene oxide is 2 to 70, preferably 2 to 40, more preferably 3 to 35, and particularly preferably 10 to 35, is an example of the polyoxyethylene castor oils that suitably exhibit the effect of the present invention. Particularly, polyoxyethylene castor oil in which the average number of moles of added ethylene oxide is 2 to 35, preferably 2 to 30, more preferably 2 to 20, and particularly preferably 2 to 12, is an example of the polyoxyethylene castor oils that suitably exhibit the effects of spreading a tear film lipid layer and stabilizing the tear.

In the present invention, these polyoxyethylene castor oils may be used singly or in any combination of two or more. Note that polyoxyethylene castor oil used in the present invention is a compound that is different from and can be distinguished from polyoxyethylene hydrogenated castor oil obtained by addition polymerization of hydrogenated castor oil with ethylene oxide.

The content of the component (A) in the aqueous ophthalmic composition of the present invention is not particularly limited and is suitably determined according to the kind of the component (A), the kind and content of the components (B) and (C) used in combination with the component (A), and the application, preparation form, usage, etc. of the aqueous ophthalmic composition. For example, the total content of the component (A) is 0.0001 to 5 w/v %, preferably 0.001 to 4 w/v %, more preferably 0.002 to 3 w/v %, even more preferably 0.005 to 2 w/v %, particularly preferably 0.01 to 1 w/v %, and more particularly preferably 0.05 to 0.5 w/v % based on the total amount of the aqueous ophthalmic composition of the present invention.

The above content of the component (A) is preferable to further improve the effect of spreading a tear film lipid layer, the effect of stabilizing the tear, and the effect of enhancing the antimicrobial effectiveness in the aqueous ophthalmic composition. When the content of the component (A) is as stated above, the component (C) described below can more effectively attain the effect of reducing foaming, the effect of reducing the defoaming time, and the effect of reducing the odor.

(2) Polyethylene Glycol Monostearate (Polyoxyl Stearate)

In addition to the component (A), the aqueous ophthalmic composition of the present invention contains polyethylene glycol monostearate (component (B)). The excellent effect of the present invention as described above is exhibited by using the components (A) and (B) in combination with (C) at least one member selected from the group consisting of sesame oil, castor oil, vitamin A, and chlorobutanol, which are described below.

Polyethylene glycol monostearate is a known compound also called macrogol stearate, polyethylene glycol stearate, or polyoxyl stearate, and several kinds of polyethylene glycol monostearates having a different average number of moles of added ethylene oxide are known. In the present invention, the average number of moles of added ethylene oxide in polyoxyl stearate used as the component (B) may be about 2 to about 150. Specific examples include polyoxyl stearate 140 in which the average number of moles of added ethylene oxide is 140, polyoxyl stearate 70 in which the average number of moles of added ethylene oxide is 70, polyoxyl stearate 55 in which the average number of moles of added ethylene oxide is 55, polyoxyl stearate 45 in which the average number of moles of added ethylene oxide is 45, polyoxyl stearate 40 in which the average number of moles of added ethylene oxide is 40, polyoxyl stearate 35 in which the average number of moles of added ethylene oxide is 35, polyoxyl stearate 30 in which the average number of moles of added ethylene oxide is 30, polyoxyl stearate 25 in which the average number of moles of added ethylene oxide is 25, polyoxyl stearate 23 in which the average number of moles of added ethylene oxide is 23, polyoxyl stearate 10 in which the average number of moles of added ethylene oxide is 10, polyoxyl stearate 9 in which the average number of moles of added ethylene oxide is 9, polyoxyl stearate 4 in which the average number of moles of added ethylene oxide is 4, and polyoxyl stearate 2 in which the average number of moles of added ethylene oxide is 2.

Of these, polyoxyl stearate in which the average number of moles of added ethylene oxide is 2 to 150, preferably 2 to 80, more preferably 10 to 70, even more preferably 10 to 60, and particularly preferably 20 to 60, is an example of the polyoxyl stearates that suitably exhibit the effect of the present invention.

In the present invention, these polyoxyl stearates may be used singly or in any combination of two or more.

The content of the component (B) in the aqueous ophthalmic composition of the present invention is not particularly limited and is suitably determined according to the kind of the component (B), the content of the components (A) and (C) used in combination with the component (B), and the application, preparation form, usage, etc. of the aqueous ophthalmic composition. For example, the total content of the component (B) is 0.0001 to 10 w/v %, preferably 0.0005 to 5 w/v %, more preferably 0.001 to 4 w/v %, even more preferably 0.005 to 3 w/v %, particularly preferably 0.01 to 2.5 w/v %, and still more preferably 0.05 to 2.5 w/v % based on the total amount of the aqueous ophthalmic composition of the present invention.

The above content of the component (B) is preferable to further improve the effect of spreading a tear film lipid layer, the effect of stabilizing the tear, and the effect of enhancing the antimicrobial effectiveness in the aqueous ophthalmic composition. When the content of the component (B) is as stated above, the component (C) described below can more effectively attain the effect of reducing foaming, the effect of reducing the defoaming time, and the effect of reducing the odor.

The content ratio of the component (B) to the component (A) in the aqueous ophthalmic composition of the present invention is suitably determined according to the kinds of the components (A) and (B), and the application, preparation form, usage, etc. of the aqueous ophthalmic composition. For example, the total content of the component (B) is 0.001 to 1,000 parts by weight, preferably 0.005 to 500 parts by weight, more preferably 0.01 to 200 parts by weight, even more preferably 0.05 to 50 parts by weight, particularly preferably 0.1 to 10 parts by weight, and more particularly preferably 0.1 to 5 parts by weight based on 1 part by weight of the total content of the component (A) contained in the aqueous ophthalmic composition of the present invention.

When the content ratio of the component (B) to the component (A) is as stated above, the present invention can be more effective.

(3) Sesame Oil, Castor Oil, Vitamin A, and Chlorobutanol

The aqueous ophthalmic composition of the present invention contains at least one member (component (C)) selected from the group consisting of sesame oil, castor oil, vitamin A, and chlorobutanol in addition to the components (A) and (B). Accordingly, the excellent effect of the present invention as described above is exhibited by using the components (A), (B), and (C) in combination.

Sesame oil means a vegetable oil obtained from seeds of plants belonging to the genus *sesamum* of the family Pedaliaceae, e.g., *Sesamumindicum Linne* (Pedaliaceae).

Sesame oil used in the present invention is not particularly limited as long as it is a pharmacologically (pharmaceutically) or physiologically acceptable oil in the field of medicine. Sesame oil obtained from seeds by using a known exploitation method or known purification method, commercially available sesame oil, or the like can be used.

Castor oil means a vegetable oil obtained from seeds of plants belonging to the genus *ricinus* of the family Euphorbiaceae, e.g., *Ricinus communis Linne* (Euphorbiaceae).

Castor oil used in the aqueous ophthalmic composition of the present invention is not particularly limited as long as it is a pharmacologically (pharmaceutically) or physiologically acceptable oil in the field of medicine. Castor oil obtained from seeds by using a known exploitation method or known purification method, commercially available sesame oil, or the like can be used.

Vitamin A is one of fat-soluble vitamins and an essential nutrient for human body. Vitamin A is a substance having vitamin A activity, and any of natural and synthetic products can be used.

Although vitamin A used in the present invention is not particularly limited as long as it is pharmacologically (pharmaceutically) or physiologically acceptable in the field of medicine, specific examples thereof include retinol, retinal, retinoic acid, a derivative and salt thereof.

Examples of derivative forms of vitamin A include retinol palmitate, retinol acetate, retinol butyrate, retinol propionate, retinol octylate, retinol laurate, retinol oleate, retinol linolenate, retinal, retinoic acid, methyl retinoate, ethyl retinoate, retinol retinoate, 6-tocopheryl retinoate, α-tocopheryl retinoate, and β-tocopheryl retinoate.

Although salt forms of vitamin A are not particularly limited as long as the salts are pharmacologically (pharmaceutically) or physiologically acceptable in the field of medicine, specific examples thereof include organic acid salts such as monocarboxylic acid salts (e.g., an acetate, a trifluoroacetate, a butyrate, a palmitate, and a stearate), polycarboxylic acid salts (e.g., a fumarate, a maleate, a succinate, and a malonate), oxycarboxylic acid salts (e.g., a lactate, a tartarate, and a citrate), and organic sulfonic acid salts (e.g., a methanesulfonate, a toluenesulfonate, and a tosilate); inorganic acid salts (e.g., a hydrochloride, a sulfate, a nitrate, a hydrobromide, and a phosphate); organic base salts (e.g., salts with organic amines such as methylamine, triethylamine, triethanolamine, morpholine, piperazine, pyrrolidine, tripyridine, and picoline); and inorganic base salts such as an ammonium salt and salts with alkali metals (e.g., sodium and potassium), alkaline-earth metals (e.g., calcium and magnesium), or aluminum or other metals.

Vitamin A may be a product isolated from natural materials such as animal sources or a chemically synthesized product. Vitamin A may also be used in the form of a vitamin A oil, which is a solution of vitamin A in an oil. The vitamin A oil may be a natural oil extracted and purified from animals or a solution of vitamin A in a vegetable oil or the like.

These vitamin A forms may be used singly or in any combination of two or more. Among these vitamin A forms, retinol acetate, retinol palmitate, and a vitamin A oil are preferably exemplified in order to further improve the effect of reducing the defoaming time.

Chlorobutanol is a known compound also called 1,1,1-trichloro-2-methyl-2-propanol and may be synthesized by a known method or can be obtained as a commercially available product.

The content of the component (C) in the aqueous ophthalmic composition of the present invention is not particularly limited and is suitably determined according to the kind of the component (C), the kind and content of the components (A) and (B) used in combination with the component (C), and the application, preparation form, usage, etc. of the aqueous ophthalmic composition. For example, the total content of the component (C) is 0.0001 to 5 w/v %, preferably 0.0002 to 1 w/v %, more preferably 0.0005 to 0.5 w/v %, particularly preferably 0.001 to 0.5 w/v %, and still more preferably 0.01 to 0.5 w/v % based on the total amount of the aqueous ophthalmic composition of the present invention.

As known to those skilled in the art, the amount of vitamin A is expressed in International Units (IU). For example, as well known in the art, 1 IU of vitamin A corresponds to about 0.30 μg of retinol, about 0.34 μg of retinol acetate, or about 0.55 μg of retinol palmitate.

When the content of vitamin A is expressed in IU, the total content of vitamin A is 200 to 5,000,000 IU/100 mL, preferably 500 to 1,000,000 IU/100 mL, more preferably 1,000 to 500,000 IU/100 mL, and particularly preferably 2,000 to 100,000 IU/100 mL based on the total amount of the aqueous ophthalmic composition of the present invention.

The above content of the component (C) is preferable to further improve the effect of spreading a tear film lipid layer, the effect of stabilizing the tear, and the effect of enhancing the antimicrobial effectiveness. The effect of reducing foaming, the effect of reducing the defoaming time, and the effect of reducing the odor are effectively exhibited.

The content ratio of the component (C) to the component (A) in the aqueous ophthalmic composition of the present invention is not particularly limited and is suitably determined according to the kinds of the components (A) and (C), and the application, preparation form, usage, etc., of the aqueous ophthalmic composition. For example, the total content of the component (C) is 0.00002 to 10,000 parts by weight, preferably 0.0001 to 1,000 parts by weight, more preferably 0.0002 to 200 parts by weight, even more preferably 0.0005 to 50 parts by weight, particularly preferably 0.001 to 50 parts by weight, still more preferably 0.01 to 10 parts by weight, and yet still more preferably 0.1 to 2 parts by weight based on 1 part by weight of the total content of the component (A) contained in the aqueous ophthalmic composition of the present invention.

When the content ratio of the component (C) to the component (A) is as stated above, the present invention can be more effective.

The content ratio of the component (C) to the component (B) in the aqueous ophthalmic composition of the present invention is not particularly limited and is suitably determined according to the kinds of the components (B) and (C), and the application, preparation form, usage, etc., of the aqueous ophthalmic composition. For example, the total content of the component (C) is 0.00002 to 10,000 parts by weight, preferably 0.0001 to 1,000 parts by weight, more preferably 0.0002 to 200 parts by weight, even more preferably 0.0005 to 50 parts by weight, particularly preferably 0.001 to 50 parts by weight, still more preferably 0.005 to 10 parts by weight, and yet still more preferably 0.01 to 2 parts by weight based on 1 part by weight of the total content of the component (B) contained in the aqueous ophthalmic composition of the present invention.

When the content ratio of the component (C) to the component (B) is as stated above, the present invention can be more effective.

(4) Buffer

The aqueous ophthalmic composition of the present invention preferably further contains a buffer (component (D)) in addition to the components (A) to (C). This can make the present invention more effective.

A buffer that is preferably added to the aqueous ophthalmic composition of the present invention is not particularly limited as long as it is a pharmacologically (pharmaceutically) or physiologically acceptable buffer in the field of medicine. Examples of such a buffer include boric acid buffers, phosphoric acid buffers, carbonic acid buffers, citric acid buffers, acetic acid buffers, tris buffers, aspartic acids, aspartates, and epsilon-aminocaproic acids. These buffers may be used singly or in any combination of two or more.

Examples of boric acid buffers which may be used include boric acid and/or boric acid salts such as alkali metal borate and alkaline-earth metal borate. Examples of phosphoric acid buffers which may be used include phosphoric acid and/or phosphoric acid salts such as alkali metal phosphate and alkaline-earth metal phosphate. Examples of carbonic acid buffers which may be used include carbonic acid and/or carbonic acid salts such as alkali metal carbonate and alkaline-earth metal carbonate. Examples of citric acid buffers which may be used include citric acid and/or citric acid salts such as alkali metal citrate and alkaline-earth metal citrate. A hydrate may also be used for each of the boric acid buffer, the phosphoric acid buffer, the carbonic acid buffer, and the citric acid buffer.

More specifically, examples of the boric acid buffer include boric acids (orthoboric acid, metaboric acid, tetraboric acid, etc.) or salts thereof (sodium borate, potassium tetraborate, potassium metaborate, ammonium borate, borax, etc.); examples of the phosphoric acid buffer include phosphoric acid or salts thereof (disodium hydrogen phosphate, sodium dihydrogen phosphate, potassium dihydrogen phosphate, trisodium phosphate, dipotassium phosphate, calcium monohydrogen phosphate, calcium dihydrogen phosphate, etc.); examples of the carbonic acid buffer include carbonic acid or salts thereof (sodium bicarbonate, sodium carbonate, ammonium carbonate, potassium carbonate, calcium carbonate, potassium bicarbonate, magnesium carbonate, etc.); examples of the citric acid buffer include citric acid or salts thereof (sodium citrate, potassium citrate, calcium citrate, sodium dihydrogen citrate, disodium citrate, etc.); examples of the acetic acid buffer include acetic acid or salts thereof (ammonium acetate, potassium acetate, calcium acetate, sodium acetate, etc.); and aspartic acid or salts thereof (sodium aspartate, magnesium aspartate, potassium aspartate, etc.). Of these buffers, a boric acid buffer (specifically, combination of boric acid and borax) and a phosphoric acid buffer (specifically, combination of disodium hydrogen phosphate and sodium dihydrogen phosphate) are preferred.

When the aqueous ophthalmic composition of the present invention contains the buffer as the component (D), the content thereof is suitably determined according to the kind of the buffer, the kinds and contents of other components, and the application, preparation form, usage, etc. of the aqueous ophthalmic composition. For example, the total content of the component (D) is 0.01 to 10 w/v %, preferably 0.05 to 8 w/v %, more preferably 0.1 to 5 w/v %, even more preferably 0.2 to 3 w/v %, and particularly preferably 0.5 to 2.5 w/v % based on the total amount of the aqueous ophthalmic composition of the present invention. Within these ranges, the effect of the present invention can be more significantly exhibited.

(5) Surfactant Other than Components (A) and (B)

The aqueous ophthalmic composition of the present invention preferably further contains a surfactant (component (E)) other than the components (A) and (B). This can make the present invention more effective.

The surfactant as the component (E) is not particularly limited as long as it is a pharmacologically (pharmaceutically) or physiologically acceptable surfactant in the field of medicine. The surfactant may be any of a nonionic surfactant, an amphoteric surfactant, an anionic surfactant, and a cationic surfactant.

Specific examples of the nonionic surfactant include POE sorbitan fatty acid esters such as POE (20) sorbitan monolaurate (polysorbate 20), POE (20) sorbitan monopalmitate (polysorbate 40), POE (20) sorbitan monostearate (polysorbate 60), POE (20) sorbitan tristearate (polysorbate 65), and POE (20) sorbitan monooleate (polysorbate 80); POE hydrogenated castor oils such as POE (40) hydrogenated castor oil (polyoxyethylene hydrogenated castor oil 40) and POE (60) hydrogenated castor oil (polyoxyethylene hydrogenated castor oil 60); POE alkyl ethers such as POE (9) lauryl ether; POE-POP alkyl ethers such as POE (20) POP (4) cetyl ether; and polyoxyethylene-polyoxypropylene block copolymers such as POE (196) POP (67) glycol (Poloxamer 407 or Pluronic F127) and POE (200) POP (70) glycol. In the compounds listed above, each of the numbers in the parentheses shows the number of moles of the added compounds.

Specific examples of the amphoteric surfactant include alkyldiaminoethylglycine or salts thereof (e.g., hydrochloride).

Specific examples of the cationic surfactant include benzalkonium chloride and benzethonium chloride.

Specific examples of the anionic surfactant include alkylbenzene sulfonate, alkyl sulfate, polyoxyethylene alkyl sulfate, aliphatic α-sulfomethyl ester, and α-olefin sulfonic acid.

Preferable examples of the surfactant as the component (E) include nonionic surfactants, more preferably POE sorbitan fatty acid esters, POE hydrogenated castor oils, and POE-POP block copolymers, and particularly preferably polysorbate 80, polyoxyethylene hydrogenated castor oil 60, and Poloxamer 407.

In the aqueous ophthalmic composition of the present invention, these surfactants as the component (E) may be used singly or in any combination of two or more.

When the aqueous ophthalmic composition of the present invention contains the surfactant as the component (E), the content thereof is suitably determined according to the kind of the surfactant, the kinds and contents of other components, and the application, preparation form, usage, etc. of the aqueous ophthalmic composition. For example, the total content of the component (E) is 0.001 to 3 w/v %, preferably 0.005 to 2 w/v %, more preferably 0.01 to 1 w/v %, and particularly preferably 0.05 to 1 w/v % based on the total amount of the aqueous ophthalmic composition of the present invention. Within these ranges, the effect of the present invention can be more significantly exhibited.

(6) Other Components

As long as the aqueous ophthalmic composition of the present invention attains the effect of the present invention, the aqueous ophthalmic composition may contain, in addition to the aforementioned components, a suitable amount of various pharmacologically active components and/or biologically active components singly or in a combination. Specifically, such components include, but are not limited to, the following components for use in ophthalmic preparations:

antihistaminic or antiallergic agents such as diphenhydramine hydrochloride and chlorphenylamine maleate;

decongestants such as tetrahydrozoline hydrochloride, naphazoline hydrochloride, naphazoline sulfate, epinephrine hydrochloride, ephedrine hydrochloride, and methylephedrine hydrochloride;

vitamins such as flavin adenine dinucleotide sodium, cyanocobalamin, pyridoxine hydrochloride, pantenol, calcium pantothenate, and tocopherol acetate;

amino acids such as potassium aspartate, magnesium aspartate, epsilon-aminocaproic acid, and sodium chondroitin sulfate;

antiphlogistics such as zinc sulfate, zinc lactate, bromfenac sodium, dipotassium glycyrrhizate, pranoprofen, allantoin, sodium azulene sulfonate, berberine chloride, berberine sulfate, and lysozyme chloride; and other agents such as sodium hyaluronate, sulfamethoxazole, and sulfamethoxazole sodium.

Further, in the aqueous ophthalmic composition of the present invention, as long as the effect of the present invention is attained, a suitable amount of one or more additives selected from various additives can be suitably added by a standard method according to the application, preparation form, etc. of the aqueous ophthalmic composition. Typical components include the following additives:

sugars such as cyclodextrin;

sugar alcohols such as xylitol, sorbitol, and mannitol, wherein these compounds may be in any of the d form, l form, or dl form;

antiseptics, disinfectants, and antibacterial agents such as benzalkonium chloride, benzethonium chloride, polyhexanide hydrochloride, alkyldiaminoethylglycine hydrochloride, sodium benzoate, ethanol, chlorhexidine gluconate, sorbic acid, potassium sorbate, methyl paraoxybenzoate, ethyl paraoxybenzoate, propyl paraoxybenzoate, and butyl paraoxybenzoate;

thickening agents and thickeners such as sodium alginate, methylcellulose, carboxymethyl cellulose, hydroxyethyl cellulose, hydroxypropyl methylcellulose, carboxyvinyl polymer, polyvinyl alcohol, polyvinyl pyrrolidone, and macrogol 4000;

tonicity agents such as sodium chloride and potassium chloride;

stabilizing agents such as dibutylhydroxytoluene, trometamol (trishydroxymethylaminomethane), sodium hydrogen sulfite, and sodium sulfite; and chelating agents such as disodium ethylenediaminetetraacetate (sodium edetate).

As the water used in the aqueous ophthalmic composition of the present invention, pharmacologically (pharmaceutically) or physiologically acceptable water in the field of medicine can be used. Specific examples of the water include distilled water, water, purified water, sterile purified water, water for injection, and distilled water for injection. These definitions are based on the Japanese Pharmacopoeia, 16th revision.

(7) Physical Properties of Aqueous Ophthalmic Composition

The pH of the aqueous ophthalmic composition of the present invention is not particularly limited as long as it is within a pharmacologically (pharmaceutically) or physiologically acceptable range in the field of medicine. For example, the pH of the aqueous ophthalmic composition of the present invention is in the range of 4.0 to 9.5, preferably in the range of 5.0 to 9.0, and more preferably in the range of 5.5 to 8.5.

The osmotic pressure of the aqueous ophthalmic composition of the present invention is not particularly limited as long as it is within a range acceptable to the living body. For example, the osmotic pressure ratio of the aqueous ophthalmic composition of the present invention is 0.5 to 5.0, preferably 0.6 to 3.0, more preferably 0.7 to 2.0, and particularly preferably 0.9 to 1.55. The osmotic pressure can be adjusted using an inorganic salt, polyhydric alcohol, sugar alcohol, sugar, etc., according to a known method in the technical field of the present invention. The osmotic pressure ratio is the ratio of the osmotic pressure of a sample to 286 mOsm (osmotic pressure of 0.9 w/v % aqueous sodium chloride solution) based on the Japanese Pharmacopoeia, 16th revision, and can be measured with reference to the osmotic measurement method (freezing point depression method) described in the Japanese Pharmacopoeia. As for the reference solution for measuring the osmotic pressure ratio (0.9 w/v % sodium chloride solution), after sodium chloride (standard reagent according to the Japanese Pharmacopoeia) is dried at 500 to 650° C. for 40 to 50 minutes, the sodium chloride is allowed to cool in a desiccator (silica gel), and 0.900 g of the resultant is accurately measured. The resultant is then dissolved in purified water, thus preparing 100 mL of the solution with accuracy. Alternatively, a commercially available reference solution for measuring the osmotic pressure ratio (0.9 w/v % sodium chloride solution) can be used.

The viscosity of the aqueous ophthalmic composition of the present invention is not particularly limited as long as it is within a range acceptable to the living body. For example, the viscosity at 25° C., which is measured by a rotation viscometer (RE-550 type viscosity meter, manufactured by TOKI SANGYO CO., LTD., rotor: 1°34'×24) is 0.01 to 1,000 mPa·s, preferably 0.05 to 100 mPa·s, and more preferably 0.1 to 10 mPa·s.

(8) Applications and Method for Preparation of Aqueous Ophthalmic Composition

The dosage form of the aqueous ophthalmic composition of the present invention is not particularly limited as long as it can be used in the field of ophthalmology. The dosage form is preferably liquid. Specific examples of the aqueous ophthalmic composition of the present invention include eye drops (also called ophthalmic solutions or ophthalmic drugs) [note that examples of the eye drops include artificial tears and also include eye drops that can be instilled into eyes during use of contact lenses], eye washes (also called collyriums or eye lotions) [note that examples of the eye washes include eye washes that can wash eyes during use of contact lenses], solutions for wearing a contact lens, and contact lens care products (contact lens disinfecting solutions, contact lens storage solutions, contact lens cleaning solutions, contact lens cleaning and storage solutions, and contact lens disinfecting, cleaning, and storage solutions (contact lens multipurpose solutions)). The aqueous ophthalmic composition of the present invention ensures a reduced defoaming time, and low variation in the drip amount during use. Therefore, the aqueous ophthalmic composition of the present invention is preferably used in eye drops and solutions for wearing a contact lens that are used in a particularly small amount each time compared to other dosage forms and that are vulnerable to variations in the amount of drops due to foam. During the production of the aqueous ophthalmic composition of the present invention, foreign matter detection can be easily performed because the defoaming time is reduced. In particular, the aqueous ophthalmic composition of the present invention is suitable as eye drops or eye washes, which are pharmaceuticals requiring foreign matter detection.

Because the antimicrobial effectiveness of the aqueous ophthalmic composition of the present invention is enhanced, the composition has excellent antiseptic effect. For this reason, the aqueous ophthalmic composition of the present invention is preferably used as a multidose aqueous ophthalmic composition, i.e., an aqueous ophthalmic composition, which is used more than once after the product is opened. The aqueous ophthalmic composition can be stably stored for a few days or a few weeks or longer. Therefore, the aqueous ophthalmic composition of the present invention is suitable for use as eye drops or eye washes that are required to be strictly hygienic for pharmaceutical purposes.

As the container that holds the aqueous ophthalmic composition of the present invention, a container that can be generally used to hold an aqueous ophthalmic composition can be used. The container may be made of glass or plastic. When a plastic container is used to hold the aqueous ophthalmic composition of the present invention, although the constituent materials of the plastic container are not particularly limited, for example, polyethylenenaphthalate, polyarylate, polyethylene terephthalate, polypropylene, polyethylene, and polyimide can be used alone or in a mixture of two or more. Examples of the material include copolymers that contain other polyester units or imide units, in addition to any one of ethylene-2,6-naphthalate units, arylate units, ethylene terephthalate units, propylene units, ethylene units, and imide units, which is contained as a main component. In the present invention, for example, a polyethylene terephthalate container indicates a container in which polyethylene terephthalate is contained in an amount of 50 w/w % or more based on the weight of the total weight of the constituent materials of the container.

The structure, constituent materials, etc., of a container spout periphery such as a nozzle mounted on a container holding the aqueous ophthalmic composition of the present invention are not particularly limited. The structure of the container spout periphery such as a nozzle may be a generally applicable structure as a spout (e.g., nozzle) of a container for ophthalmologic compositions (e.g., container for eye drops), and the nozzle may be integrally or separately formed with the container. Examples of the constituent materials of the spout periphery or spout (e.g., nozzle) include those mentioned in the constituent materials of the plastic containers.

In particular, to further improve flexibility, cost, and/or an effect of reducing variation in the drip amount, a spout that contains polyethylene or polypropylene as a constituent material is preferable. Examples of polyethylene include high-density polyethylene and low-density polyethylene; particularly, of these, a spout containing low-density polyethylene as a constituent material is preferable. As a spout, a nozzle used for a container of eye drops is preferable.

As a preferable combination of a container that holds the aqueous ophthalmic composition of the present invention and a container spout periphery, it is possible to use a combination of a polyethylene terephthalate container and a polyethylene container spout periphery, more preferably, a combination of a polyethylene terephthalate eye drop container and a polyethylene nozzle, and particularly preferably, a combination of a polyethylene terephthalate eye drop container and a low-density polyethylene nozzle. Such a combination can significantly exhibit the effect of reducing variation in the drip amount in the present invention.

Since the aqueous ophthalmic composition of the present invention can reduce the defoaming time, reduce variation in the drip amount during use, and can be instilled into an eye in a specific amount per use, it is particularly suitably used as eye drops containing a pharmacologically active component and/or a biologically active component. Such eye drops can be used as eye drops for dry eyes, decongestant eye drops, antibacterial eye drops, anti-inflammatory eye drops, eye drops for relieving itchy eyes, eye drops for relieving eye strain, eye drops for relieving eye dryness, etc. In particular, the present invention is excellent in effect of stabilizing the tear and effect of spreading a tear film lipid layer. Therefore, the aqueous ophthalmic composition of the present invention is particularly useful as eye drops for dry eyes or eye drops for relieving eye dryness.

From a different viewpoint, the present invention also provides use of (A) polyoxyethylene castor oil, (B) polyethylene glycol monostearate, and (C) at least one member selected from the group consisting of sesame oil, castor oil, vitamin A, and chlorobutanol for production of an aqueous ophthalmic composition.

From another different viewpoint, the present invention also provides use of a composition as an aqueous ophthalmic composition, the composition comprising (A) polyoxyethylene castor oil, (B) polyethylene glycol monostearate, and (C) at least one member selected from the group consisting of sesame oil, castor oil, vitamin A, and chlorobutanol.

From still another different viewpoint, the present invention provides a composition for use as an aqueous ophthalmic composition, the composition comprising (A) polyoxyethylene castor oil, (B) polyethylene glycol monostearate, and (C) at least one member selected from the group consisting of sesame oil, castor oil, vitamin A, and chlorobutanol.

2. Method for Reducing Foaming

As described above, in the aqueous ophthalmic composition of the present invention, by containing the components (A), (B), and (C), the foaming of the aqueous ophthalmic composition can be reduced, and consequently, dissolution check, foreign matter detection, and other steps can be performed in a short time, so that production efficiency can be significantly improved.

From still another different viewpoint, the present invention provides a method for reducing foaming of an aqueous ophthalmic composition, comprising adding (A) polyoxyethylene castor oil, (B) polyethylene glycol monostearate, and (C) at least one member selected from the group consisting of sesame oil, castor oil, vitamin A, and chlorobutanol to the aqueous ophthalmic composition.

The present invention also provides a method for reducing foaming of an aqueous ophthalmic composition, comprising supplementing an aqueous ophthalmic composition comprising (A) polyoxyethylene castor oil and (B) polyethylene glycol monostearate with (C) at least one member selected from the group consisting of sesame oil, castor oil, vitamin A, and chlorobutanol.

In these methods, as long as the components (A), (B), and (C) are coexisted, they may be added at the same time or separately, and the order thereof is not particularly limited. The kinds of the components (A), (B) and (C) to be used, the contents (or addition contents) thereof and the ratio thereof, the kinds and contents (or addition contents) of components added other than the above, the preparation form of the aqueous ophthalmic composition, the kind and combination of the container, the embodiment method, and the like are the same as in the "1. Aqueous Ophthalmic Composition" section above.

In particular, the methods described above are suitably used when the aqueous ophthalmic composition is used as eye drops or a solution for wearing a contact lens.

In the present specification, whether or not foaming of an aqueous ophthalmic composition is reduced can be determined according to the method in the Examples described below.

3. Method for Reducing Defoaming Time

As described above, in the aqueous ophthalmic composition of the present invention, by containing the components (A), (B), and (C), the defoaming time of the aqueous ophthalmic composition can be reduced, and consequently, variation in the drip amount during use can be reduced.

Therefore, from still another different viewpoint, the present invention provides a method for reducing the defoaming time of an aqueous ophthalmic composition, comprising adding (A) polyoxyethylene castor oil, (B) polyethylene glycol monostearate, and (C) at least one member selected from the group consisting of sesame oil, castor oil, vitamin A, and chlorobutanol to the aqueous ophthalmic composition.

The present invention also provides a method for reducing the defoaming time of an aqueous ophthalmic composition, comprising supplementing an aqueous ophthalmic composition comprising (A) polyoxyethylene castor oil and (B) polyethylene glycol monostearate with (C) at least one member selected from the group consisting of sesame oil, castor oil, vitamin A, and chlorobutanol.

The present invention also provides a method for reducing variations in the drip amount of an aqueous ophthalmic composition during use, comprising adding (A) polyoxyethylene castor oil, (B) polyethylene glycol monostearate, and (C) at least one member selected from the group consisting of sesame oil, castor oil, vitamin A, and chlorobutanol to the aqueous ophthalmic composition.

The present invention also provides a method for reducing variations in the drip amount of an aqueous ophthalmic composition during use, comprising supplementing an aqueous ophthalmic composition comprising (A) polyoxyethylene castor oil and (B) polyethylene glycol monostearate with (C) at least one member selected from the group consisting of sesame oil, castor oil, vitamin A, and chlorobutanol.

In these methods, as long as the components (A), (B), and (C) are coexisted, they may be added at the same time or separately, and the order thereof is not particularly limited. The kinds of the components (A), (B) and (C) to be used, the contents (or addition contents) thereof and the ratio thereof, the kinds and contents (or addition contents) of components added other than the above, the preparation form of the aqueous ophthalmic composition, the kind and combination of the container, the embodiment method, and the like are the same as in the "1. Aqueous Ophthalmic Composition" section above.

In particular, the methods described above are suitably used when the aqueous ophthalmic composition is used as eye drops or a solution for wearing a contact lens.

In the present specification, whether or not the defoaming time of an aqueous ophthalmic composition is reduced can be determined according to the method in the Examples described below.

4. Method for Enhancing Antimicrobial Effectiveness

As described above, in the aqueous ophthalmic composition of the present invention, by containing the components (A), (B), and (C), the antimicrobial effectiveness of the aqueous ophthalmic composition can be enhanced.

Therefore, from still another different viewpoint, the present invention provides a method for enhancing the antimicrobial effectiveness of an aqueous ophthalmic composition, comprising adding (A) polyoxyethylene castor oil, (B) polyethylene glycol monostearate, and (C) at least one member selected from the group consisting of sesame oil, castor oil, vitamin A, and chlorobutanol to the aqueous ophthalmic composition.

In this method, as long as the components (A), (B), and (C) are coexisted, they may be added at the same time or separately, and the order thereof is not particularly limited. The kinds of the components (A), (B) and (C) to be used, the contents (or addition contents) thereof and the ratio thereof, the kinds and contents (or addition contents) of components added other than the above, the preparation form of the aqueous ophthalmic composition, the kind and combination of the container, the embodiment method, and the like are the same as in the "1. Aqueous Ophthalmic Composition" section above.

Of these methods, the aqueous ophthalmic composition is preferably used as a multidose aqueous ophthalmic composition, i.e., an aqueous ophthalmic composition used more than one time after the product is opened. Examples of such an aqueous ophthalmic composition include multidose eye drops, multidose eye washes, multidose solutions for wearing a contact lens, and multidose contact lens care products.

In the present specification, whether or not the antimicrobial effectiveness of an aqueous ophthalmic composition is enhanced can be determined according to the method in the Examples described below.

5. Method for Stabilizing Tear

As described above, in the aqueous ophthalmic composition of the present invention, by containing the components (A), (B), and (C), the tear can be stabilized, and consequently, dry eyes or eye dryness can be relieved.

Therefore, from still another different viewpoint, the present invention provides a method for imparting an effect of stabilizing the tear to an aqueous ophthalmic composition, comprising adding (A) polyoxyethylene castor oil, (B) polyethylene glycol monostearate, and (C) at least one member selected from the group consisting of sesame oil, castor oil, vitamin A, and chlorobutanol to the aqueous ophthalmic composition.

The present invention also provides a method for imparting an effect of relieving dry eyes or eye dryness to an aqueous ophthalmic composition, comprising adding (A) polyoxyethylene castor oil, (B) polyethylene glycol monostearate, and (C) at least one member selected from the group consisting of sesame oil, castor oil, vitamin A, and chlorobutanol to the aqueous ophthalmic composition. The aqueous ophthalmic composition obtained by this method is suitable for dry eyes or for relieving eye dryness.

In these methods, as long as the components (A), (B), and (C) are coexisted, they may be added at the same time or separately, and the order thereof is not particularly limited. The kinds of the components (A), (B) and (C) to be used, the contents (or addition contents) thereof and the ratio thereof, the kinds and contents (or addition contents) of components added other than the above, the preparation form of the aqueous ophthalmic composition, the kind and combination of the container, the embodiment method, and the like are the same as in the "1. Aqueous Ophthalmic Composition" section above.

In particular, the methods described above are suitably used when the aqueous ophthalmic composition is used as eye drops or a solution for wearing a contact lens.

In the present specification, whether or not an effect of stabilizing the tear is imparted to an aqueous ophthalmic composition can be determined according to the method in the Examples described below.

6. Method for Spreading Tear Film Lipid Layer

As described above, in the aqueous ophthalmic composition of the present invention, by containing the components (A), (B), and (C), a tear film lipid layer can be easily spread in a short time after blinking, that is, the aqueous ophthalmic composition of the present invention is high in effect of spreading a tear film lipid layer and thus can relieve dry eyes or eye dryness.

Therefore, from still another different viewpoint, the present invention provides a method for imparting an effect of spreading a tear film lipid layer to an aqueous ophthalmic composition, comprising adding (A) polyoxyethylene castor oil, (B) polyethylene glycol monostearate, and (C) at least one member selected from the group consisting of sesame oil, castor oil, vitamin A, and chlorobutanol to the aqueous ophthalmic composition. The aqueous ophthalmic composition obtained by this method is suitable for dry eyes or for relieving eye dryness.

In the method, as long as the components (A), (B), and (C) are coexisted, they may be added at the same time or separately, and the order thereof is not particularly limited. The kinds of the components (A), (B) and (C) to be used, the contents (or addition contents) thereof and the ratio thereof, the kinds and contents (or addition contents) of components added other than the above, the preparation form of the aqueous ophthalmic composition, the kind and combination of the container, the embodiment method, and the like are the same as in the "1. Aqueous Ophthalmic Composition" section above.

In particular, the methods described above are suitably used when the aqueous ophthalmic composition is used as eye drops or a solution for wearing a contact lens.

In the present specification, whether or not an effect of spreading a tear film lipid layer is imparted to an aqueous ophthalmic composition can be determined according to the method in the Examples described below.

7. Odor Reducing Method

As described above, in the aqueous ophthalmic composition of the present invention, by containing the components (A), (B), and (C), the odor of the aqueous ophthalmic composition can be reduced.

Therefore, from still another different viewpoint, the present invention provides a method for reducing the odor of an aqueous ophthalmic composition, comprising adding (A) polyoxyethylene castor oil, (B) polyethylene glycol monostearate, and (C) at least one member selected from the group consisting of sesame oil, castor oil, vitamin A, and chlorobutanol to the aqueous ophthalmic composition.

The present invention also provides a method for reducing the odor of an aqueous ophthalmic composition, comprising supplementing an aqueous ophthalmic composition comprising (A) polyoxyethylene castor oil and (B) polyethylene glycol monostearate with (C) at least one member selected from the group consisting of sesame oil, castor oil, vitamin A, and chlorobutanol.

In these methods, as long as the components (A), (B), and (C) are coexisted, they may be added at the same time or separately, and the order thereof is not particularly limited. The kinds of the components (A), (B) and (C) to be used, the contents (or addition contents) thereof and the ratio thereof, the kinds and contents (or addition contents) of components added other than the above, the preparation form of the aqueous ophthalmic composition, the kind and combination of the container, the embodiment method, and the like are the same as in the "1. Aqueous Ophthalmic Composition" section above.

In particular, the methods described above are suitably used when the aqueous ophthalmic composition is used as eye drops or a solution for wearing a contact lens.

In the present specification, whether or not the odor of an aqueous ophthalmic composition is reduced can be determined according to the method in the Examples described below.

EXAMPLES

Examples and Test Examples are given below to illustrate the present invention in detail; however, the present invention is not limited to these Examples and the like. In Examples and Test Examples below, polyoxyethylene castor oil 35 that conforms to the standard for polyoxyethylene castor oil in Japanese Pharmaceutical Excipients 2003 and in which the average number of moles of added ethylene oxide is 35 is used, polyoxyethylene castor oil 10 that conforms to the standard for polyoxyethylene castor oil in Japanese Pharmaceutical Excipients 2003 and in which the average number of moles of added ethylene oxide is 10 is used, polyoxyl stearate 40 that conforms to the standard for polyoxyl stearate in Japanese Pharmaceutical Excipients 2003 and in which the average number of moles of added ethylene oxide is 40 is used, and polysorbate 80 and polyoxyethylene hydrogenated castor oil 60 (HCO60) that conform to the standards in the Japanese Pharmacopoeia are used.

Test Example 1

Foaming-Reducing Test

Aqueous ophthalmic compositions shown in the following Table 1 were prepared by a standard method and used as test solutions. An effect of reducing foaming was evaluated by the following method for each of the aqueous ophthalmic compositions of Examples 1 to 5 and Comparative Example 1 and 2.

Specifically, each of the aqueous ophthalmic compositions of Examples 1 to 5 and Comparative Examples 1 and 2 in an amount of 30 mL was placed in individual 50-mL glass centrifuge tube with a cap. The tubes were shaken 1,500 times using RECIPAD SHAKER SR-2w (TAITEC). Immediately after shaking, a foam part and an aqueous solution part were confirmed by visual observation, and the height of the foam part was measured and used as an initial foaming value. The initial foaming value of Comparative Example was normalized to 100%, and the foaming rate (%) was calculated with the formula below.

Foaming rate (%)=(initial foaming (height) of each test solution)/(initial foaming(height) of corresponding Comparative Example)×100

The corresponding Comparative Examples are, specifically, Comparative Example 1 for Examples 1, 3, and 4, and Comparative Example 2 for Examples 2 and 5.

Figure 1:
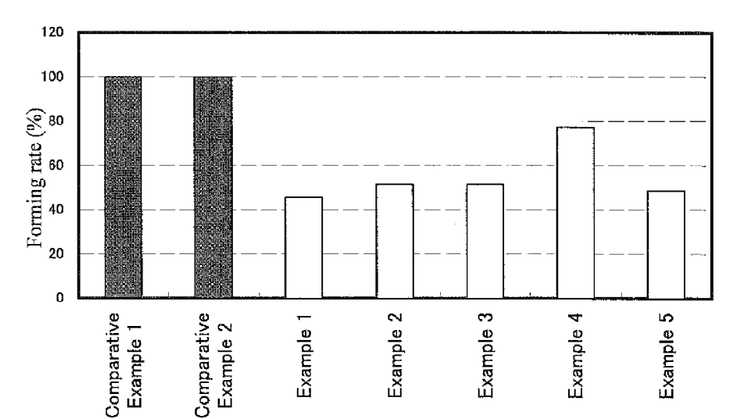
FIG. 1 is a graph showing the results (foaming rates (%)) of Test Example 1.

The results are shown in FIG. 1. As shown in FIG. 1, Comparative Examples 1 and 2, which are free of the component (C), significantly foamed immediately after the shaking was completed, but initial foaming of Examples 1 to 5, to which sesame oil, castor oil, or retinol palmitate was added as the component (C), was significantly reduced.

TABLE 1

Units: w/v %

|  | Example 1 | Example 2 | Example 3 | Example 4 | Example 5 | Comparative Example 1 | Comparative Example 2 |
|---|---|---|---|---|---|---|---|
| Polyoxyethylene castor oil 35 | 0.5 | 0.5 | 0.5 | 0.5 | 0.5 | 0.5 | 0.5 |
| Polyoxyl stearate 40 | 2.5 | 0.5 | 2.5 | 2.5 | 0.5 | 2.5 | 0.5 |
| Sesame oil | 0.1 | 0.1 | — | — | — | — | — |
| Castor oil | — | — | 0.1 | — | — | — | — |
| Retinol palmitate | — | — | — | 50,000 IU | 50,000 IU | — | — |
| 2Na hydrogen phosphate 12$H_2O$ | 0.5 | 0.5 | 0.5 | 0.5 | 0.5 | 0.5 | 0.5 |
| Sodium dihydrogen phosphate | 0.07 | 0.07 | 0.07 | 0.07 | 0.07 | 0.07 | 0.07 |
| Purified water | Balance | Balance | Balance | Balance | Balance | Balance | Balance |
| Total amount | 100 mL | 100 mL | 100 mL | 100 mL | 100 mL | 100 mL | 100 mL |
| pH | 7.0 | 7.0 | 7.0 | 7.0 | 7.0 | 7.0 | 7.0 |

Test Example 2

Defoaming Acceleration Test

Aqueous ophthalmic compositions shown in the following Tables 2-1 and 2-2 were prepared by a standard method and used as test solutions. An effect of defoaming acceleration was evaluated by the following method for each of the aqueous ophthalmic compositions of Examples 6 to 13 and Comparative Examples 3 to 6.

Specifically, each of the aqueous ophthalmic compositions of Examples 6 to 13 and Comparative Examples 3 to 6 in an amount of 30 mL was placed in individual 50-mL glass centrifuge tube. The tubes were shaken 1,500 times using RECIPAD SHAKER SR-2w (TAITEC). Immediately after shaking, the height of the foam part was visually measured. While how the foam decreased over time was observed, the period of time when the measured height of the foam part decreased to half of that immediately after shaking was determined as the foam half-life (minutes). The foam half-life (minutes) in each corresponding Comparative Example was normalized to 100%, and the ratio (%) of the time taken for defoaming in each test solution to decrease to half was calculated with the formula below.

Ratio (%) of time taken for defoaming=(foam half-life (minutes) in each test solution)/(foam half-life(minutes) in corresponding Comparative Example)×100

The corresponding Comparative Examples are, specifically, Comparative Example 3 for Examples 6 to 9 and Comparative Example 4, and Comparative Example 5 for Examples 10 to 13 and Comparative Example 6. The results are also shown in Tables 2-1 and 2-2.

TABLE 2-1

Units: w/v %

| | Example 6 | Example 7 | Example 8 | Example 9 | Comparative Example 3 | Comparative Example 4 |
|---|---|---|---|---|---|---|
| Polyoxyethylene castor oil 35 | 0.5 | 0.5 | 0.5 | 0.5 | 0.5 | — |
| Polyoxyl stearate 40 | 2.5 | 2.5 | 2.5 | 2.5 | 2.5 | 3.0 |
| Sesame oil | 0.1 | — | — | — | — | — |
| Castor oil | — | 0.1 | — | — | — | — |
| Retinol palmitate | — | — | 50,000 IU | — | — | — |
| Chlorobutanol | — | — | — | 0.4 | — | — |
| 2Na hydrogen phosphate 12H$_2$O | 05 | 0.5 | 0.5 | 0.5 | 0.5 | 0.5 |
| Sodium dihydrogen phosphate | 0.07 | 0.07 | 0.07 | 0.07 | 0.07 | 0.07 |
| Purified water | Balance | Balance | Balance | Balance | Balance | Balance |
| Total amount | 100 mL | 100 mL | 100 mL | 100 mL | 100 mL | 100 mL |
| pH | 7.0 | 7.0 | 7.0 | 7.0 | 7.0 | 7.0 |
| Ratio (%) of time taken for defoaming | 63 | 54 | 69 | 14 | 100 | 53 |

TABLE 2-2

Units: w/v %

| | Example 10 | Example 11 | Example 12 | Example 13 | Comparative Example 5 | Comparative Example 6 |
|---|---|---|---|---|---|---|
| Polyoxyethylene castor oil 35 | 0.5 | 0.5 | 0.5 | 0.5 | 0.5 | — |
| Polyoxyl stearate 40 | 0.5 | 0.5 | 0.5 | 0.5 | 0.5 | 1.0 |
| Sesame oil | 0.1 | — | — | — | — | — |
| Castor oil | — | 0.1 | — | — | — | — |
| Retinol palmitate | — | — | 50,000 IU | — | — | — |
| Chlorobutanol | — | — | — | 0.4 | — | — |
| 2Na hydrogen phosphate 12H$_2$O | 05 | 0.5 | 0.5 | 0.5 | 0.5 | 0.5 |
| Sodium dihydrogen phosphate | 0.07 | 0.07 | 0.07 | 0.07 | 0.07 | 0.07 |
| Purified water | Balance | Balance | Balance | Balance | Balance | Balance |
| Total amount | 100 mL | 100 mL | 100 mL | 100 mL | 100 mL | 100 mL |
| pH | 7.0 | 7.0 | 7.0 | 7.0 | 7.0 | 7.0 |
| Ratio (%) of time taken for defoaming | 88 | 44 | 69 | 15 | 100 | 36 |

As shown in Tables 2-1 and 2-2, the time taken for defoaming was significantly longer when polyoxyl stearate was used in combination with polyoxyethylene castor oil (Comparative Examples 3 and 5) than when polyoxyl stearate was used alone (Comparative Examples 4 and 6). In contrast, Examples 6 to 13, to which sesame oil, castor oil, retinol palmitate, or chlorobutanol was added as the component (C), allowed the time taken for defoaming to be significantly reduced and also allowed acceleration of defoaming.

Test Example 3

Odor Measurement Test

Aqueous ophthalmic compositions having the formulations shown in the following Tables 3-1 and 3-2 were prepared by a standard method and used as test solutions. An odor measurement test was performed by the following method for each of the aqueous ophthalmic compositions of Examples 14 to 17 and Comparative Examples 7 to 9.

Specifically, each of the aqueous ophthalmic compositions of Examples 14 to 17 and Comparative Examples 7 to 9 in an amount of 15 mL was placed in individual 10 polyethylene terephthalate eye-drop containers (15 mL in volume). After a polyethylene nozzle was attached to each container, five containers were stored at 4° C. for 1 month, and the remaining five containers were stored at 60° C. for 2 weeks. After the storage, a drop of each aqueous ophthalmic composition was put on the arm of each tester and spread over an area equal to that of a ten-yen coin. The tester smelled the area and evaluated the odor using VAS method. That is, a straight line 10 cm in length was used, and one (0 mm) of both ends of the line represented "complete absence of odor," and the other end (100 mm) "intolerable odor." The tester marked a point on the line that matches the odor of each aqueous ophthalmic composition. The distance (mm) from the 0 mm end was measured and used as the odor score. Five testers were selected as being sensitive to odor and performed the test. The results are also shown in Tables 3-1 and 3-2.

TABLE 3-1

Units: w/v %

|  | Example 14 | Example 15 | Comparative Example 7 | Comparative Example 8 |
|---|---|---|---|---|
| Polyoxyethylene castor oil 35 | 0.5 | 0.5 | — | 0.5 |
| Polyoxyl stearate 40 | 2.5 | 2.5 | 2.5 | 2.5 |
| Castor oil | 0.1 | — | — | — |
| Retinol palmitate | — | 50,000 IU | — | — |
| Boric acid | 0.5 | 0.5 | 0.5 | 0.5 |
| Borax | 0.008 | 0.008 | 0.008 | 0.008 |
| Purified water | Balance | Balance | Balance | Balance |
| Total amount | 100 mL | 100 mL | 100 mL | 100 mL |
| Odor (4° C. storage) | 34.8 | 10.2 | 3.2 | 59 |

TABLE 3-2

Units: w/v %

|  | Example 16 | Example 17 | Comparative Example 9 |
|---|---|---|---|
| Polyoxyethylene castor oil 35 | 0.5 | 0.5 | 0.5 |
| Polyoxyl stearate 40 | 0.5 | 0.5 | 0.5 |
| Castor oil | 0.1 | — | — |
| Retinal palmitate | — | 50,000 IU | — |
| Boric acid | 0.5 | 0.5 | 0.5 |
| Borax | 0.008 | 0.008 | 0.008 |
| Purified water | Balance | Balance | Balance |
| Total amount | 100 mL | 100 mL | 100 mL |
| Odor (4° C. storage) | 26.2 | 20.2 | 51.02 |
| Odor (60° C. storage) | 37 | 25.8 | 63.2 |

As shown in Table 3-1, it was demonstrated that a combination of polyoxyethylene castor oil and polyoxyl stearate made the odor of the test solution worse (Comparative Examples 7 and 8), but the addition of castor oil or retinol palmitate significantly reduced the odor (Examples 14 to 17). In addition, Table 3-2 showed that in the test where Examples 16 and 17 and Comparative Example 9 were stored at 60° C. for changes over time, the odor of Comparative Example 9 became much worse than that after the storage at 4° C., but such deterioration of the odor over time was significantly reduced by the coexistence of castor oil or retinol palmitate in the test solution (Examples 16 and 17). In general, changes over time caused by heat at 60° C. for 2 weeks correspond to those caused by heat at 25° C. for about 1.5 years.

Test Example 4

Antimicrobial Effectiveness Test

Aqueous ophthalmic compositions shown in the following Table 4 were prepared by a standard method. A antimicrobial effectiveness test was performed by the following method for each of the aqueous ophthalmic compositions of Examples 18 and Comparative Examples 10 to 13.

First, *Staphylococcus aureus* (ATCC6538) was inoculated on the surface of a soybean-casein digest slant medium and cultured at 33° C. for 24 hours. The cultured cells were aseptically collected using a platinum loop and suspended in an appropriate amount of sterile physiological saline to prepare a bacterial suspension containing viable cells at about $1\times10^6$ CFU/mL. The viable microbial count in the suspension was measured by performing separate culture. Subsequently, each of the aqueous ophthalmic compositions of Example 18 and Comparative Examples 10 to 13 in an amount of 5 mL was placed in individual 15-mL CORNING conical tube (PET). The *Staphylococcus aureus* bacterial suspension (suspension in physiological saline) was inoculated into each of the aqueous ophthalmic compositions so that the viable microbial count (final concentration) was about $10^4$ CFU/mL, and stirred thoroughly to prepare samples. The samples were stored at 23° C. for 96 hours while shielded from light. After this 96-hour-period ended, each of the samples containing viable cells was adjusted to have an adequate concentration for counting, seeded on a lecithin, polysorbate 80, soybean-casein digest agar medium (SCDLP agar medium) and cultured overnight at 33° C. Thereafter, the number of observed colonies was counted to determine the viable microbial count for each of the samples. The results are also shown in Table 4.

TABLE 4

Units: w/v %

|  | Example 18 | Comparative Example 10 | Comparative Example 11 | Comparative Example 12 | Comparative Example 13 |
|---|---|---|---|---|---|
| Polyoxyethylene castor oil 35 | 0.5 | — | — | 0.5 | 0.5 |
| Polyoxyl stearate 40 | 2.5 | — | 2.5 | — | — |
| Retinol palmitate | 50,000 IU | — | — | — | 50,000 IU |
| 2Na hydrogen phosphate 12H$_2$O | 0.5 | 0.5 | 0.5 | 0.5 | 0.5 |
| Sodium dihydrogen phosphate | 0.07 | 0.07 | 0.07 | 0.07 | 0.07 |
| Purified water | Balance | Balance | Balance | Balance | Balance |
| Total amount | 100 mL | 100 mL | 100 mL | 100 mL | 100 mL |
| pH | 7 | 7 | 7 | 7 | 7 |
| Viable microbial count (cfu/mL) after 96 hours | 1400 | 23000 | 18000 | 69000 | 55000 |

As shown in Table 4, the antimicrobial effectiveness of the test solution containing either polyoxyethylene castor oil or polyoxyl stearate in combination with a phosphate buffer (Comparative Examples 11 and 12) was almost unchanged or rather lower than that of the test solution with only a phosphate buffer (Comparative Example 10). The antimicrobial effectiveness of the test solution containing polyethylene castor oil and retinol palmitate in combination with a phosphate buffer (Comparative Example 13) was also lower than that of the test sample with only a phosphate buffer (Comparative Example 10). Entirely unexpectedly, however, Example 18 containing a combination of the three components polyoxyethylene castor oil, polyoxyl stearate, and retinol palmitate showed significant enhancement of antimicrobial effectiveness.

Test Example 5

Lipid Layer Spreading Test

Aqueous ophthalmic compositions shown in the following Tables 5-1 and 5-2 were prepared by a standard method. A lipid layer-spreading test was performed by the following method for each of the aqueous ophthalmic compositions of Examples 19 to 21 and Comparative Examples 14 to 19.

First, 2.5 mL of physiological saline (OTSUKA NORMAL SALINE) was dispensed to each well of a Corning 6-well plate, and then 1 mL of each test solution was gently added dropwise to each well. After 5 minutes, the wells were photographed and evaluated for the spreading of lipid. The results are shown in Tables 5-1 and 5-2.

Of the formulations shown in Tables 5-1 and 5-2, Sudan Black (manufactured by Wako Pure Chemical Industries, Ltd.) is a colorant for facilitating the observation of lipid spreading.

Scores for Lipid Layer Spreading:

A lipid layer uniformly spreads over the whole area... ⊙
The central part of a lipid layer observed is slightly uneven, or a slight lipid layer adsorbs on the wall surface... ○
The central part of a lipid layer is uneven, and a slight lipid layer adsorbs on the wall surface... Δ
An entirely uneven lipid layer is formed... X

TABLE 5-1

Units: w/v %

| | Example 19 | Example 20 | Example 21 | Comparative Example 14 | Comparative Example 15 | Comparative Example 16 |
|---|---|---|---|---|---|---|
| Polyoxyethylene castor oil 10 | 0.4 | — | 0.4 | — | — | — |
| Polyoxyethylene castor oil 35 | — | 0.4 | — | — | — | — |
| Polyoxyl stearate 40 | 0.1 | 0.1 | 0.1 | 0.5 | — | — |
| HCO60 | — | — | — | — | 0.5 | — |
| TO10M | — | — | — | — | — | 0.5 |
| Sesame oil | 0.1 | 0.1 | — | 0.1 | 0.1 | 0.1 |
| Castor oil | — | — | 0.1 | — | — | — |
| Sudan Black | 0.003 | 0.003 | 0.003 | 0.003 | 0.003 | 0.003 |
| Purified water | Balance | Balance | Balance | Balance | Balance | Balance |
| Total amount | 100 mL | 100 mL | 100 mL | 100 mL | 100 mL | 100 mL |
| Score | ⊙ | ○ | ○ | X | X | X |

TABLE 5-2

Units: w/v %

| | Comparative Example 17 | Comparative Example 18 | Comparative Example 19 |
|---|---|---|---|
| Polyoxyethylene castor oil 10 | — | 0.4 | — |
| Polyoxyethylene castor oil 35 | — | — | 0.4 |
| Polyoxyl stearate 40 | 0.1 | 0.1 | 0.1 |
| HCO60 | — | — | — |
| TO10M | — | — | — |
| Tyloxapol | 0.4 | — | — |
| Sesame oil | 0.1 | — | — |
| Castor oil | — | — | — |
| Soybean oil | — | 0.1 | 0.1 |
| Sudan Black | 0.003 | 0.003 | 0.003 |
| Purified water | Balance | Balance | Balance |
| Total | 100 mL | 100 mL | 100 mL |
| Score | X | X | X |

As shown in Table 5-1, the test solution containing a combination of polyoxyethylene castor oil and polyoxyl stearate allowed sesame oil or castor oil to uniformly spread on the physiological saline (Examples 19 to 21). However, even though the test solution contained a nonionic surfactant, the whole of the lipid layer was uneven when the test solution was free of either the component (A) or (B) (Comparative Examples 14 to 17). In addition, even though the test solution contained the components (A) and (B), the whole of the lipid layer was uneven when soybean oil was used instead of the component (C) (Comparative Examples 18 and 19). Therefore, it was demonstrated that aqueous ophthalmic compositions containing all the components (A) to (C) significantly exhibit the lipid layer-spreading effect.

Test Example 6

Tear Stabilizing Test

Aqueous ophthalmic compositions having the formulations shown in the following Table 6 were prepared by a standard method. A tear stabilizing test was performed by the following method for each of the aqueous ophthalmic compositions of Example 22 and Comparative Example 20.

Specifically, each of the aqueous ophthalmic compositions of Example 22 and Comparative Example 20 in an amount of 15 mL was placed in individual 15-mL polyethylene terephthalate eye drop container, to which a polyethylene nozzle was attached. Before instillation, the subject blinked and then opened eyes, 5 seconds after which how the tear film on the eye surface was breaking up was recorded using a tear dynamics observation system DR-1 (manufactured by Kowa Company, Ltd.). Next, immediately after instillation of a drop of each aqueous ophthalmic composition, the subject blinked and then opened eyes, 5 seconds after which how the tear film on the eye surface was breaking up was similarly recorded using DR-1. In addition, 5 minutes after instillation of a drop of each aqueous ophthalmic composition, the subject blinked and then opened eyes, 5 seconds and 60 seconds respectively, after which how the tear film on the eye surface was breaking up was similarly recorded using DR-1. The results were also shown in Table 6.

It is conceivable that the slighter the breakup of the tear film, the more stabilized the tear film and hence the more relieved eye dryness will be.

Scores for Breakup of Tear Film:

Absence of breakup. . . −
Presence of slight breakup. . . +
Presence of moderate breakup. . . ++
Presence of severe breakup. . . +++
Impossible to keep eyes open because of eye dryness. . . ++++

In addition, irritation immediately after instillation and dryness sensation at the time of rising in the next morning were evaluated by VAS method. That is, a straight line 10 cm in length was used, and one (0 cm) of both ends of the line represented "completely no irritation," and the other end (10 cm) "maximum irritation that has ever been experienced." The tester marked a point on the line that matches the irritation felt upon the instillation of each aqueous ophthalmic composition. The distance from the 0 cm end was measured and used as the irritation score. Dryness sensation in the next morning was also evaluated in a similar way. A straight line 10 cm in length was used, and one (0 cm) of both ends of the line represented "completely no dryness sensation," and the other end (10 cm) "maximum dryness sensation that has ever been experienced." Three testers (n=3) performed the evaluation for dryness sensation scores. The results are also shown in Table 6.

TABLE 6

Units: w/v %

| | Example 22 | Comparative Example 20 |
|---|---|---|
| Polyoxyethylene castor oil 10 | 0.3 | — |
| Polyoxyl stearate 40 | 0.075 | — |
| Polysorbate 80 | — | 0.375 |
| Sesame oil | 0.1 | 0.1 |
| Propylene glycol | 0.1 | 0.1 |
| EDTA | 0.01 | 0.01 |
| Boric acid | 1.4 | 1.4 |
| Borax | 0.4 | 0.4 |
| Purified water | Balance | Balance |
| Total amount | 100 mL | 100 mL |
| PH | 7.5 | 7.5 |
| Breakup 5 seconds after eye-opening before instillation | + | + |
| Breakup 5 seconds after eye-opening immediately after instillation | − | + |
| Breakup 5 seconds after eye-opening 5 minutes after instillation | − | + |
| Breakup 60 seconds after eye-opening 5 minutes after instillation | − | ++++ |
| Irritation immediately after instillation | 0 | 5 |
| Dryness sensation after rising in the next morning | 0 | 9 |

As shown in Table 6, Comparative Example 20 caused slight breakup immediately after the instillation, but surprisingly, Example 22 caused no breakup even at the time of 60-second eye-opening 5 minutes after the instillation, and also caused no dryness sensation even after the rising in the next morning. In addition, Comparative Example 20 caused strong irritation, but Example 22 caused no irritation.

The invention claimed is:

1. An aqueous ophthalmic composition, comprising
   (A) polyoxyethylene castor oil,
   (B) polyethylene glycol monostearate, and
   (C) at least one member selected from the group consisting of sesame oil, castor oil, vitamin A, and chlorobutanol,
   wherein a concentration ratio of the (A) polyoxyethylene castor oil to the (B) polyethylene glycol monosterate in the composition is from 4:1 to 1:5, and
   total content of component (C) is 0.01 to 10 parts by weight based on 1 part by weight of total content of component (A).

2. The aqueous ophthalmic composition according to claim 1, further comprising (D) a buffer.

3. The aqueous ophthalmic composition according to claim 1, further comprising (E) a surfactant other than components (A) and (B).

4. The aqueous ophthalmic composition according to claim 1, wherein the aqueous ophthalmic composition is eye drops, an eye wash, a solution for wearing a contact lens, or a contact lens care solution.

5. The aqueous ophthalmic composition according to claim 2, further comprising (E) a surfactant other than components (A) and (B).

6. The aqueous ophthalmic composition according to claim 2, wherein the aqueous ophthalmic composition is eye drops, an eye wash, a solution for wearing a contact lens, or a contact lens care solution.

7. The aqueous ophthalmic composition according to claim 5, wherein the aqueous ophthalmic composition is eye drops, an eye wash, a solution for wearing a contact lens, or a contact lens care solution.

8. The aqueous ophthalmic composition according to claim 1, wherein total content of component (C) is 0.00002 to 10,000 parts by weight based on 1 part by weight of total content of component (B).

9. The aqueous ophthalmic composition according to claim 3, wherein total content of component (C) is 0.00002 to 10,000 parts by weight based on 1 part by weight of total content of component (B).

10. The aqueous ophthalmic composition according to claim 1, wherein the aqueous ophthalmic composition comprises the sesame oil.

11. The aqueous ophthalmic composition according to claim 1, wherein the aqueous ophthalmic composition comprises the castor oil.

12. The aqueous ophthalmic composition according to claim 1, wherein the aqueous ophthalmic composition comprises the vitamin A.

13. The aqueous ophthalmic composition according to claim 1, wherein the aqueous ophthalmic composition comprises the chlorobutanol.

14. The aqueous ophthalmic composition according to claim 1, wherein the polyethylene glycol monostearate is selected from the group consisting of polyoxyl stearate 140, polyoxyl stearate 70, polyoxyl stearate 55, polyoxyl stearate 45, polyoxyl stearate 40, polyoxyl stearate 30, polyoxyl stearate 23, polyoxyl stearate 10, polyoxyl stearate 9 and polyoxyl stearate 2.

15. The aqueous ophthalmic composition according to claim 1, wherein
an average number of moles of added ethylene oxide in the (A) polyoxyethylene castor oil is 2 to 70, and
an average number of moles of added ethylene oxide in the (B) polyethylene glycol monostearate is 2 to 150.

16. The aqueous ophthalmic composition according to claim 1, wherein
an average number of moles of added ethylene oxide in the (A) polyoxyethylene castor oil is 2 to 40, and
an average number of moles of added ethylene oxide in the (B) polyethylene glycol monostearate is 20 to 60.

17. The aqueous ophthalmic composition according to claim 1, wherein the composition has 0.0001 to 5 w/v % of the (A) polyoxyethylene castor oil, and 0.0001 to 5 w/v % of the (B) polyethylene glycol monosterate.

18. The aqueous ophthalmic composition according to claim 1, wherein the composition has 0.01 to 1 w/v % of the (A) polyoxyethylene castor oil, and 0.01 to 2.5 w/v % of the (B) polyethylene glycol monosterate.

* * * * *